(12) United States Patent
Cho et al.

(10) Patent No.: US 6,713,631 B2
(45) Date of Patent: Mar. 30, 2004

(54) PREPARATION METHOD OF 2,2'-BI-1H-IMIDAZOLE USING GLYOXAL AND AN AMMONIUM SALT

(75) Inventors: Jin Rai Cho, Daejeon (KR); Soo Gyeong Cho, Daejeon (KR); Eun Mee Goh, Daejeon (KR); Jae Kyung Kim, Seoul (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 10/383,196

(22) Filed: Mar. 6, 2003

(65) Prior Publication Data

US 2003/0199700 A1 Oct. 23, 2003

(30) Foreign Application Priority Data

Apr. 10, 2002 (KR) ................. 10-2002-0019524

(51) Int. Cl.$^7$ ............................................ C07D 403/04
(52) U.S. Cl. .................................................. 548/313.4
(58) Field of Search ........................................ 548/313.4

(56) References Cited

PUBLICATIONS

Liu et al., Journal of Polymer Science, Part A: Polymer Chemistry, 1988, 26(11), pp. 3015–3029.*
Collier et al., Analytical Science & Technology, 1998, 11(1), pp. 8–12.*
Benjamin Fieselman, David N. Hendrick, and Galen D. Stucky, "Synthesis, Electron Paramagnetic Resonance, and Magnetic Studies of Binuclear Bis($\eta^3$–Cyclopentadienyl)Titanium(III) Compounds with Bridging Pyrazolate, Biimidazolate, and Bibenzimidazolate Anions", *Inorganic Chemistry*, vol. 17, No. 8, 1978, pp. 2078–2079.

F. Holmes, K.M. Jones, and E.G. Torrible, "Complex–Forming Agents Similar to 2,2'–Bipyridyl), Some Ligands Containing Imidazole Part. I", *J. Chemical Society*, 1961, pp. 4790–4791.

Donald P. Matthews, Jeffery P. Whitten, James R. McCarthy, "A Convenient Synthetic Route to 2,2'–Biimidazole", *Synthesis*, Apr. 1986, pp. 336–337.

* cited by examiner

*Primary Examiner*—Laura L. Stockton
(74) *Attorney, Agent, or Firm*—Scully, Scott, Murphy & Presser

(57) ABSTRACT

Disclosed is a preparation method of 2,2'-bi-1H-imidazole using glyoxal and an ammonium salt as starting materials through a safe, simple and easily controlled synthetic process with a high yield.

5 Claims, No Drawings

PREPARATION METHOD OF 2,2'-BI-1H-IMIDAZOLE USING GLYOXAL AND AN AMMONIUM SALT

BACKGROUND OF THE INVENTION

1. Field of the Invention

The present invention relates to a preparation method of 2,2'-bi-1H-imidazole.

2. Description of the Background Art 2,2'-Bi-1H-imidazole is a compound, which has been widely used as a chelating agent for a metal, an intermediate for a biologically active substance, a component of polyurethane, an intermediate for a copying toner, an intermediate for a high energy substance or the like.

A synthetic method of 2,2'-bi-1H-imidazole currently and widely used is the one proposed by B. F. Fieselmann in 1978. In this method, 20 wt % aqueous glyoxal solution is reacted with anhydrous ammonia gas to obtain 2,2'-bi-1H-imidazole in a brown-colored precipitate with 33% yield (See *Inorg. Chem.* 1978, 17, 2078). The Fieselmann's method can be represented by the following reaction scheme 1.

Reaction scheme 1

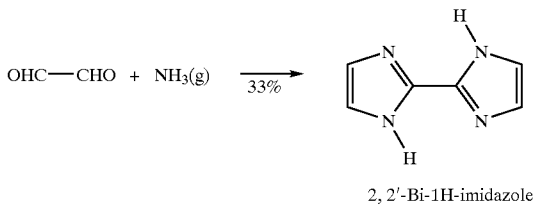

2, 2'-Bi-1H-imidazole

However, because the above method uses a toxic ammonia gas, it is difficult to control its reaction. The chemical reaction vigorously takes place around an inlet for an ammonia gas injection and then produce precipitate there, which blocks an entrance of the inlet, and accordingly, it is difficult to proceed the reaction. Besides, the ammonia should be used excessively since it is difficult to exactly determine the amount of the ammonia gas input during the synthetic process. Moreover, the yield of the desired product is only 33%.

Therefore, it is certain that the conventional preparation method of 2,2'-bi-1H-imidazole preparation method has disadvantages in aspects of safety and economical efficiency, which are necessary to be improved. Accordingly, a lot of efforts have been made to overcome such disadvantages of the conventional method, for example, by using a catalyst and the like. However, it has not been fundamentally improved yet.

SUMMARY OF THE INVENTION

Therefore, an object of the present invention is to solve the problems of the prior art and to provide a preparation method of 2,2'-bi-1H-imidazole through a simple, safe and easily controlled synthetic process with a high yield.

The above and other objects of the invention, as embodied and broadly described herein, can be achieved by using glyoxal and an ammonium salt as starting materials for obtaining 2,2'-bi-1H-imidazole.

The foregoing and other features, aspects and advantages of the present invention will become more apparent from the following detailed description of the present invention.

DETAILED DESCRIPTION OF THE INVENTION

A preparation method of 2,2'-bi-1H-imidazole of the present invention is carried out through a reaction of glyoxal with an ammonium salt represented by the following reaction scheme 2:

Reaction Scheme 2

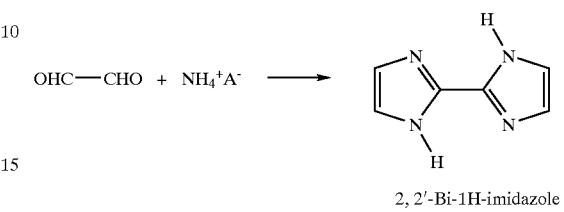

2, 2'-Bi-1H-imidazole wherein, $NH_4^+A$ represents an ammonium salt.

Hereinafter, an embodiment of carrying out the present invention will be described in more detail.

At first, a slurry containing excess amount of an ammonium salt is made by adding the ammonium salt in water. An aqueous glyoxal is then slowly added dropwise to the ammonium salt slurry while vigorously stirring. The resultant is then additionally stirred at room temperature for 0–5 hours. After the reaction is completed, an aqueous alkali solution or distilled water is then added to the reaction mixture so as to adjust its pH to be in the range of 5–7. A produced brown colored solid is then filtered, washed alternately with an organic solvent and distilled water several times and then dried, to obtain 2,2'-bi-1H-imidazole.

In the present invention, glyoxal and an ammonium salt are used as starting materials. 20 wt % aqueous glyoxal is preferably used as a material for the glyoxal. The ammonium salt used as a starting material is not specially limited to any specific compounds. Examples can include ammonium acetate, ammonium benzoate, ammonium bromide, ammonium carbonate, ammonium chloride, ammonium chromate, ammonium dichromate, ammonium formate, ammonium nitrate, ammonium oxalate, ammonium sulfamate, ammonium sulfate, ammonium sulfite, ammonium tartarate, ammonium tetrafluoroborate, ammonium thiocyanate, ammonium thiosulfate and the like.

A temperature when adding the aqueous glyoxal to the ammonium salt slurry is preferably in the range of 30–60° C. If the temperature exceeds this range, the yield of the desired product is lowered, and ammonia gas is generated caused by a decomposition of the ammonium salt. The time for adding the aqueous glyoxal to the ammonium slurry depends on a reaction condition and a quantity of the reactants, and is preferably 2–4 hours.

The alkali solution used for adjusting pH of the reaction mixture after completion of the reaction is not specially limited. Examples can include aqueous ammonia, and aqueous solutions of lithium hydroxide, sodium hydroxide, potassium hydroxide, sodium carbonate, sodium hydrogen carbonate, potassium carbonate, potassium hydrogen carbonate, sodium acetate and the like. In this case, the concentration of the alkali solution is 5–20% by weight. Distilled water can be used for neutralization instead of an alkali solution. When neutralizing, it is important not to make pH of the reaction mixture exceed 7. If pH exceeds 7, 2,2'-bi-1H-imidazole can be a metal salt so that it can be partially dissolved in water.

According to the present invention as described above, 2,2'-bi-1H-imidazole having a purity of not less than 97% can be obtained in 43–54% yield.

EXAMPLES

The present invention will be described in more detail by way of the following examples, which are not intended to limit the scope of the present invention thereto.

Example 1

130 ml of distilled water was added to 709 g of ammonium acetate (9.2 mol, 2.67 eq.) at 40° C., and 500 g of 20 wt % aqueous glyoxal (3.45 mol) was then slowly added dropwise to the resulting slurry for three hours while vigorously stirring. The resulting reaction mixture was additionally stirred for five hours at room temperature. The reaction mixture was then neutralized with aqueous ammonia so as to adjust pH to 5–7. The produced brown colored solid was filtered and then washed alternately with 500 ml of acetone and 500 ml of distilled water several times, to obtain 78.4 g (50.9% yield) of 2,2'-bi-1H-imidazole having a purity of not less than 97%.

Example 2

The same amount of glyoxal as in Example was reacted with ammonium acetate in the same manner as described in Example 1. The reaction mixture was then neutralized with 5% aqueous sodium hydroxide, instead of aqueous ammonia, to obtain 70.6 g (45.8% yield) of the desired product.

Example 3

130 ml of distilled water was added to 580 g (9.2 mol, 2.67 eq.) of ammonium formate at 50° C., and 500 g of 20 wt % aqueous glyoxal (3.45 mol) was then slowly added dropwise to the resulting slurry for one and a half hours while vigorously stirring. Immediately after the addition was finished, the reaction mixture was neutralized with aqueous ammonia so as to adjust pH to 5–7. The produced brown colored solid was filtered, and washed alternately with 500 ml of acetone and 500 ml of distilled water several times, to obtain 68.7 g (44.6% yield) of 2,2'-bi-1H-imidazole having a purity of not less than 97%.

Example 4

130 ml of distilled water was added to 959 g (6.9 mol, 2.0 eq.) of ammonium benzoate at 40° C., and 500 g of 20 wt % aqueous glyoxal (3.45 mol) was then slowly added dropwise to the resulting slurry for three hours while vigorously stirring. The resulting reaction mixture was then additionally stirred for one hour at room temperature. The reaction mixture was then neutralized with aqueous ammonia so as to adjust pH to 5–7. The produced brown colored solid was filtered, and washed alternately with 500 ml of acetone and 500 ml of distilled water several times, to obtain 66.4 g (43.1% yield) of 2,2'-bi-1H-imidazole having a purity of not less than 97%.

Example 5

120 ml of distilled water was added to 1,092 g (14.2 mol, 4.0 eq.) of ammonium acetate at 40° C., and 500 g of 20 wt % aqueous glyoxal (3.45 mol) was then slowly added dropwise to the resulting slurry for three hours while vigorously stirring. Immediately after the addition was finished, the reaction mixture was neutralized with distilled water so as to adjust pH to 5–7. The produced brown colored solid was filtered, and washed alternately with 500 ml of acetone and 500 ml of distilled water several times, to obtain 82.0 g (53.2% yield) of 2,2'-bi-1H-imidazole having a purity of not less than 97%.

2,2'-bi-1H-imidazole prepared in Examples 1 to 5 is identified with an elementary analysis and NMR, and the results are respectively shown in the following Tables 1 and 2.

TABLE 1

| Elementary Analysis | C | H | N |
|---|---|---|---|
| Calculated | 53.72 | 4.51 | 41.77 |
| Found | 53.45 | 4.30 | 38.87 |

TABLE 2

| NMR | Element | Solvent | Shift (ppm) |
|---|---|---|---|
| $^1$H NMR | $C_4$—H, $C_5$—H | $CDCl_3$ | 7.05 |
|  | $N_1$—H |  | 12.57 |
| $^{13}$C NMR | $C_4$, $C_5$ |  | 139.30 |

As described above, a preparation method of 2,2'-bi-1H-imidazole was provided through a reaction of glyoxal with an ammonium salt. The synthetic process according to the present invention is safe and simple, and can be easily controlled because only glyoxal and an ammonium salt are used as starting materials. Moreover, the present invention enables to obtain the desired product with a relatively high yield.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A preparation method of 2,2'-bi-1H-imidazole which comprises reacting glyoxal with excess amount of an ammonium salt selected from the group consisting of ammonium acetate, ammonium benzoate, ammonium bromide, ammonium carbonate, ammonium chloride, ammonium chromate, ammonium dichromate, ammonium formate, ammonium nitrate, ammonium oxalate, ammonium sulfamate, ammonium sulfate, ammonium sulfite, ammonium tartarate, ammonium tetrafluoroborate, ammonium thiocynanate and ammonium thiosulfate, wherein the reaction scheme is:

OHC—CHO + $NH_4^+A^-$ ⟶ 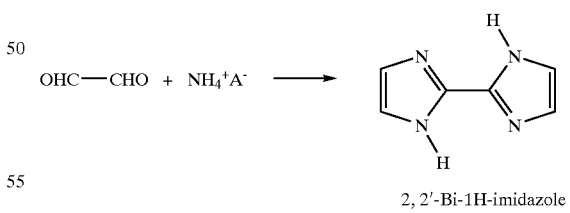

2, 2'-Bi-1H-imidazole and wherein NH4+A− represents an ammonium salt.

2. The method according to claim 1, wherein the reaction comprises the steps of:
   (a) making an ammonium salt slurry in water;
   (b) adding dropwise 20 wt % aqueous glyoxal to the ammonium salt slurry obtained in step (a) for 2–4 hours at 30–60° C.; and
   (c) stirring the reaction mixture obtained in step (b) for additional 0–5 hours at room temperature, so as to complete the reaction.

3. The method according to claim 2, further comprising a step of adjusting pH of the reaction mixture to 5–7 by adding an aqueous alkali solution or distilled water to the reaction mixture after the reaction is completed.

4. The method according to claim 3, wherein the aqueous alkali solution is consisting of aqueous ammonia, and aqueous solutions of lithium hydroxide, sodium hydroxide, potassium hydroxide, sodium carbonate, sodium hydrogen carbonate, potassium carbonate, potassium hydrogen carbonate and sodium acetic acetate.

5. The method according to claim 3, wherein a concentration of the aqueous alkali solution is 5–20% by weight.

* * * * *